United States Patent [19]

Duffett

[11] Patent Number: Plant 5,352

[45] Date of Patent: Nov. 20, 1984

[54] CHRYSANTHEMUM PLANT NAMED TEMPTER

[75] Inventor: William E. Duffett, Salinas, Calif.

[73] Assignee: Yoder Brothers, Inc., Barberton, Ohio

[21] Appl. No.: 467,862

[22] Filed: Feb. 18, 1983

[51] Int. Cl.[3] ..... A01H 5/00

[52] U.S. Cl. ..... Plt./78

[58] Field of Search ..... Plt./78

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant named Tempter having flat capitulum form; decorative capitulum type; medium yellow ray floret color; diameter across face of capitulum ranging from 90 to 120 mm. at maturity; uniform nine week photoperiodic flowering response to short days; tall plant height when grown as a pinched, disbud pot mum, and semi-spreading branching pattern.

3 Drawing Figures

The present invention comprises a new and distinct cultivar of *Chrysanthemum morifolium*, Ramat., named Tempter.

Tempter is a product of a planned sport induction program which had the objective of creating new chrysanthemum cultivars that would expand the color range of existing cultivars while retaining their other original traits.

Tempter was discovered and selected by William E. Duffett in March 1981 in a controlled environment in Salinas, Calif. as one flowering plant, a color variant within a flowering block established as rooted cuttings from stock plants which had been exposed as unrooted cuttings to an X-ray source of 1800 rads. The irradiated variety was Tempo, disclosed in U.S. Plant Pat. No. 4,505, originated by the present inventor.

The first act of a sexual reproduction of Tempter was accomplished when vegetative cuttings were taken from the initial selection in May 1981 in a controlled environment in Salinas, Calif. by a technician working under formulations established and supervised by William E. Duffett. Horticultural examination of selected units initiated November 1982 has demonstrated that the combination of characteristics as herein disclosed for Tempter are firmly fixed and are retained through successive generations of asexual reproduction.

Tempter has not been observed under all possible environmental conditions. The phenotype may vary significantly with variations in environment such as temperature, light intensity and day length. The observations, measurements and comparisons described plants grown in Salinas, Calif. and Leamington, Canada under greenhouse conditions which approximate those generally used in commercial practice.

The following traits have been repeatedly observed and are determined to be basic characteristics of Tempter which in combination distinguish this chrysanthemum as a new and distinct cultivar:

(1) Flat capitulum form;

(2) Decorative capitulum type;

(3) Medium yellow ray floret color;

(4) Diameter across face of capitulum ranging from 90 to 120 mm. at maturity;

(5) Uniform nine week photoperiodic flowering response to short days;

(6) Tall plant height, requiring 1-2 long day weeks prior to pinch and short days, and 1-2 applications of 2500 ppm B-9 after the beginning of short days to attain a flowered plant height of 25 to 35 cm.; and (7) Semi-spreading branching pattern.

The accompanying photographic drawings depict typical foliage and inflorescence characteristics of Tempter. Sheet 1 is a color photograph of a plant of Tempter grown as a pinched, disbud pot mum, with colors being as accurate as possible with renditions of this type. Sheet 2 is a black and white photograph of three views of the inflorescence of Tempter. Sheet 3 shows the leaves of Tempter in three stages of development (mature, intermediate and immature).

Of the many commercial cultivars known to the present inventor, the most similar in comparison to Tempter is Yellow Mandalay. Reference is made to attached Chart A which compares certain characteristics of Tempter to those same characteristics of Yellow Mandalay.

Yellow Mandalay differs from Tempter by its deeper yellow color which is frequently tinged bronze, more spreading branching pattern, smaller capitulum diameter, shorter plant height, and slower flowering response especially during high temperature, summer flowering periods. Yellow Mandalay is similar to Tempter in capitulum form and type.

In the following description, color references are made to The Royal Horticultural Society Color Chart. The color values were determined between 2:00 P.M. and 2:15 P.M. on Aug. 13, 1982 under 150 foot-candle light intensity at Salinas, Calif.

CLASSIFICATION

Botanical: *Chrysanthemum morifolium*, Ramat., cv TEMPTER

Commercial: Disbud and spray decorative pot mum.

INFLORESCENCE

Capitulum:

*Form.*—Flat.

*Type.*—Decorative.

*Diameter across face.*—90 To 120 mm.

Corolla of ray florets:

*Color (general tonality from a distance of three meters).*—Medium yellow.

*Color (abaxial).*—3A, 3B.

*Color (adaxial).*—4B, 4C.

*Shape.*—Oblong. Notched tip.

Corolla of disc florets:

*Color (mature).*—154C.

*Color (immature).*—149C.

Reproductive organs:

*Androecium.*—Present disc florets only; very few; scant pollen.

*Gynoecium.*—Present both ray and disc florets.

PLANT

General appearance:

*Height.*—Tall; 25 to 35 cm. given 2 long day weeks before pinch and lights out, and 1-2 applications of 2500 ppm B-9 SP after lights out.

*Branching pattern.*—Semi-spreading.

Foliage:

*Color (abaxial).*—147B.

*Color (adaxial).*—147C.

*Shape.*—Moderately lobed and serrated.

CHART A

COMPARISON OF TEMPTER AND YELLOW MANDALAY

| CULTIVAR | RAY FLORET COLOR | CAPITULUM FORM AND TYPE | BRANCHING PATTERN |
|---|---|---|---|
| TEMPTER | MEDIUM YELLOW | FLAT DECORATIVE | SEMI-SPREADING |

CHART A-continued

COMPARISON OF TEMPTER AND YELLOW MANDALAY

| | | | |
|---|---|---|---|
| YELLOW MANDALAY | DARK YELLOW (tinged bronze) | FLAT DECORATIVE | SPREADING SPREADING |

| CULTIVAR | DIAMETER ACROSS FACE OF CAPITULUM | PLANT HEIGHT | FLOWERING RESPONSE PERIOD |
|---|---|---|---|
| TEMPTER | 90 to 120 mm. | TALL 25 to 35 cm. | 9 WEEKS |
| YELLOW | 75 to 95 mm. | SHORT 20 to 30 cm. | 10 WEEKS |

COMPARISONS MADE OF PLANTS GROWN AS PINCHED DISBUD POT MUMS IN SALINAS, CALIFORNIA AND LEAMINGTON, CANADA

I claim:

1. A new and distinct cultivar of *Chrysanthemum morifolium,* Ramat., named Tempter, as described and illustrated, and particularly characterized as to uniqueness by the combined characteristics of flat capitulum form; decorative capitulum type; medium yellow ray floret color; diameter across face of capitulum ranging from 90 to 120 mm. at maturity; uniform nine week flowering response; tall plant height, and semi-spreading branching pattern.

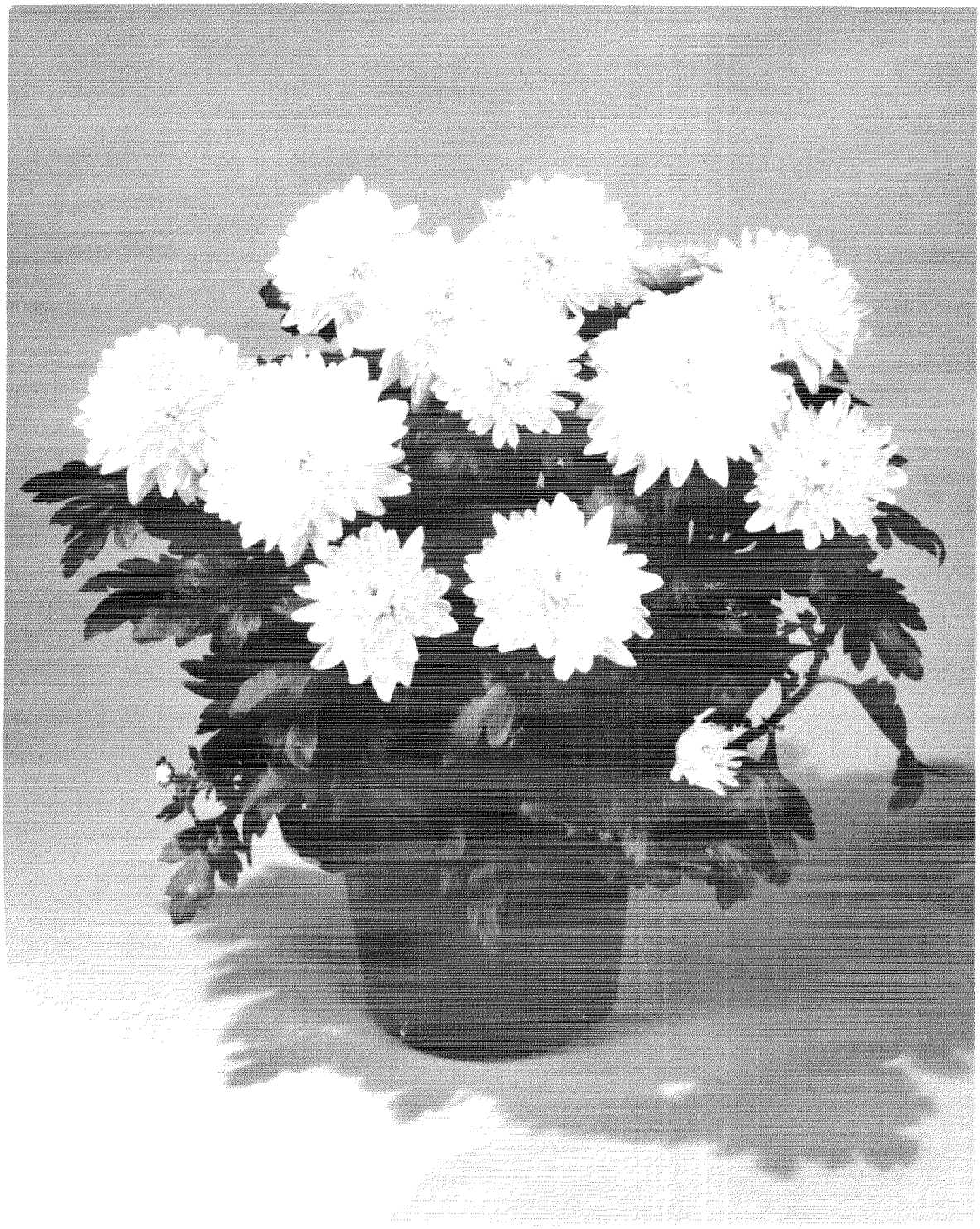

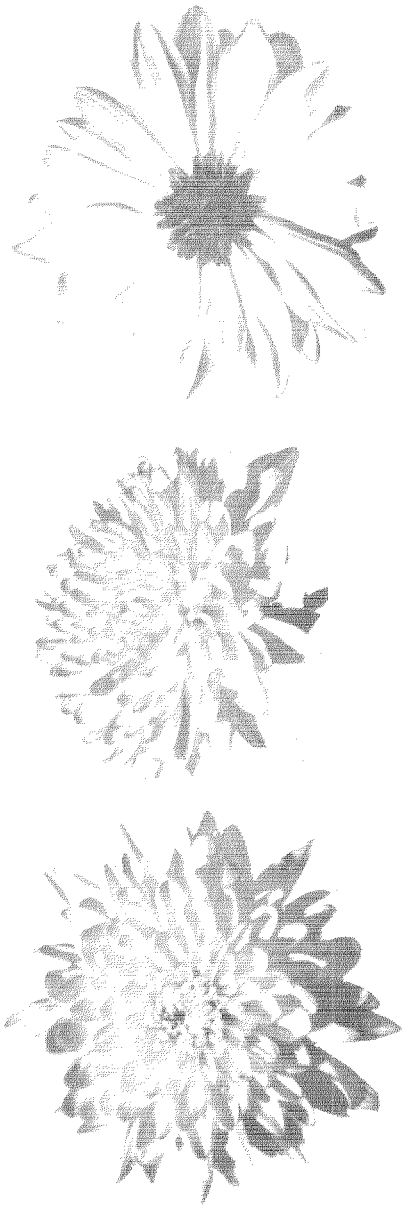

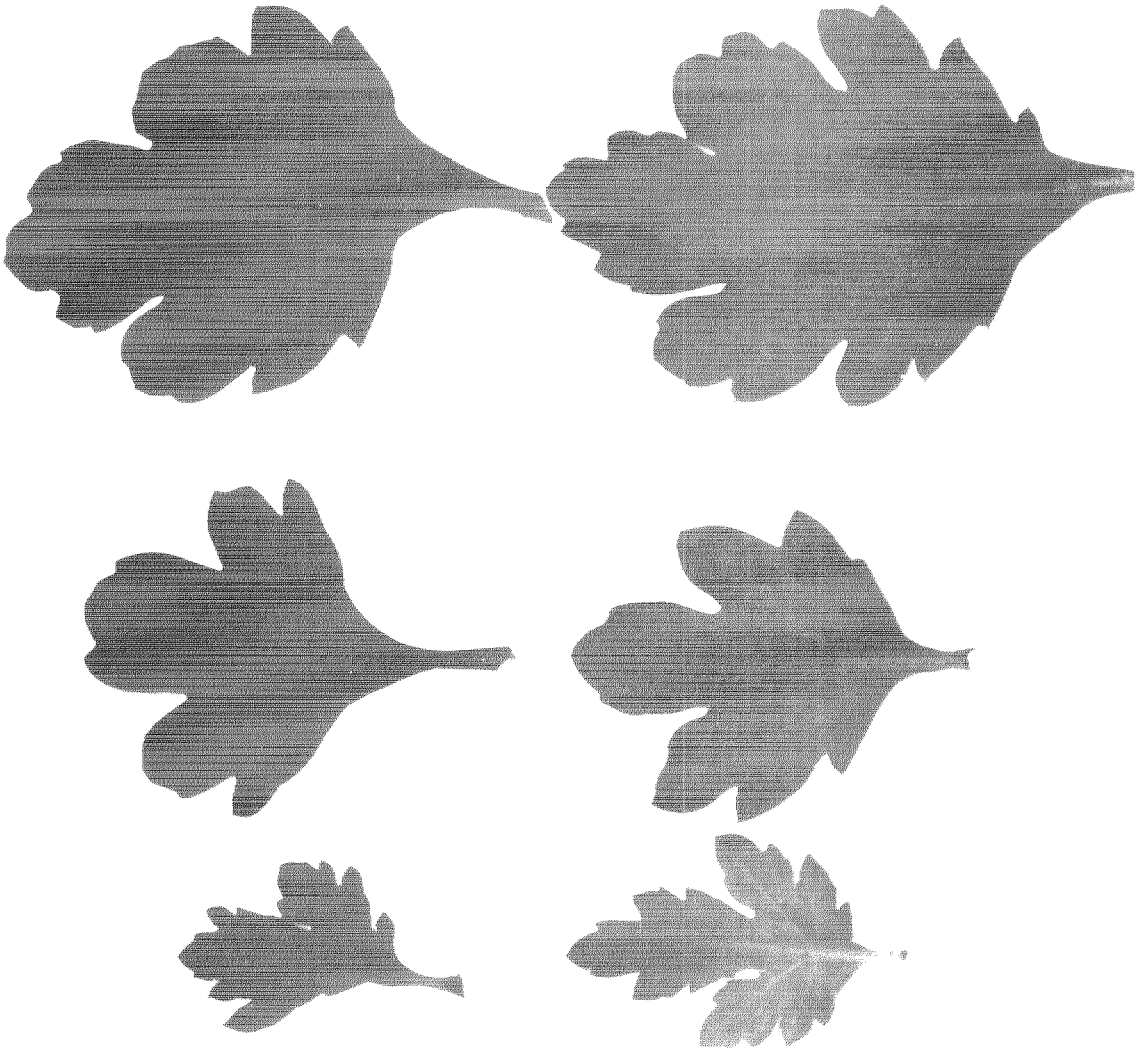

* * * * *